United States Patent [19]

Gust

[11] 4,187,850

[45] Feb. 12, 1980

[54] STOMA CENTERING APPARATUS

[76] Inventor: Charles F. Gust, Sky Harbor Estates Corp., 2959 Gulf Tobay Blvd., #422, Clearwater, Fla. 33515

[21] Appl. No.: 859,554

[22] Filed: Dec. 12, 1977

[51] Int. Cl.² ............................................. A61F 5/44
[52] U.S. Cl. .................................................. 128/283
[58] Field of Search ................. 128/283, 132 D, 348, 128/1 R

[56] References Cited

U.S. PATENT DOCUMENTS

| 1,491,011 | 4/1924 | Hodgin | 128/132 D |
| 2,684,676 | 7/1954 | Perry | 125/283 |
| 3,520,301 | 7/1970 | Fenton | 128/283 |

Primary Examiner—Robert W. Michell
Assistant Examiner—Milford A. Juten
Attorney, Agent, or Firm—Robert E. Wagner; Gerald T. Shekleton

[57] ABSTRACT

A medical-surgical method and apparatus for facilitating the replacement of ostomy appliances. A hollow cylinder, filled with sterile absorbant material is used to center the sealing ring prior to the replacement of the ostomy appliance.

6 Claims, 5 Drawing Figures

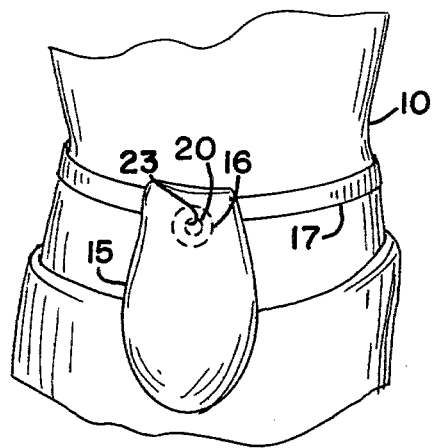
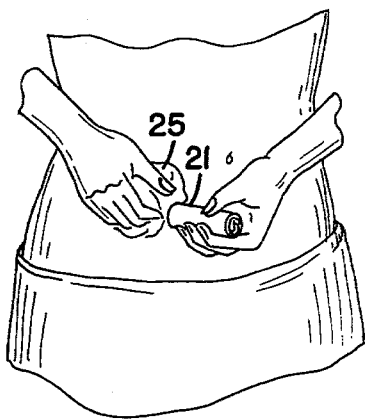
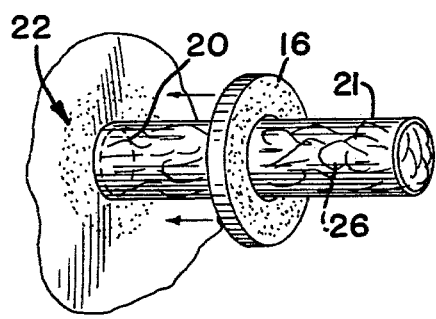
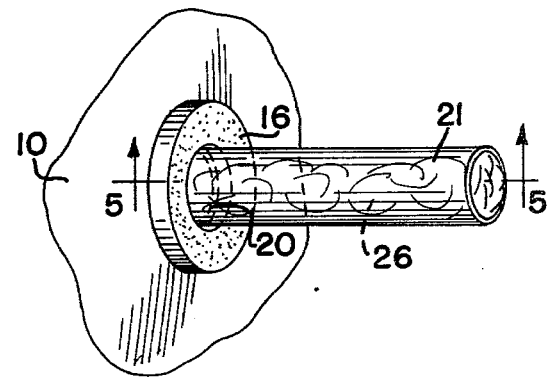
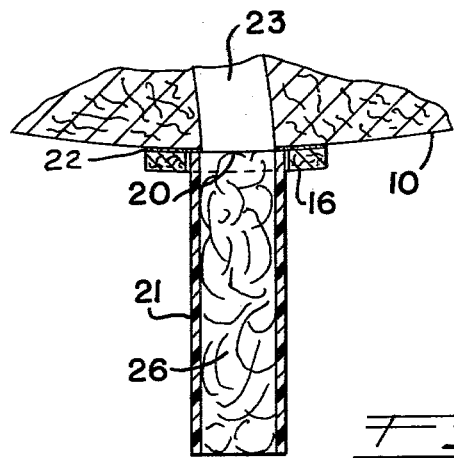

STOMA CENTERING APPARATUS

BACKGROUND OF THE INVENTION

This application relates to a medical-surgical apparatus and, in particular, to an apparatus for facilitating the replacement of a stoma bag for those people having had surgical operations for removing a bladder or colon.

In surgical operations, such as a colostomy where the colon is removed, or a cystostomy where the bladder is removed, the colon or ureter is rerouted so that waste material may exit through an artificial opening in the body known as a stoma. A stoma is connected directly to the kidney by a rerouted ureter or to the intestines by the rerouted colon and the discharge of waste matter in each instance is made through the stoma.

The new artificial opening, or stoma, made on the abdominal wall into the large bowel and termed a colostomy, has no voluntary sphincter control by the patient. In order to avoid involuntary bowel movement through the stoma, it is customary and desirable for the patient periodically to take an enema, commonly called irrigation, through the stoma. The frequency required of this irrigation is generally daily, or perhaps every second day, in order to keep the bowel free from involuntary discharges. Thus, any ostomy appliance which the patient may wear must necessarily be removed at least as often as irrigation is required.

Collection of involuntary waste seepage is by bag or other receptacle attached to the body of the patient. Good examples of such a receptacle for use after a colostomy are those taught in U.S. Pat. Nos. 2,561,906, 2,575,063 and 4,054,140. In general, these waste receptacles are mounted on a sealing ring which itself is adhesively secured to the body. It is essential that this ring be mounted directly and concentrically over the stoma and further, that it be tightly secured to the body, otherwise leakage of waste onto the surrounding skin area can occur. During removal and replacement of the ostomy appliance it becomes imperative that the area to which the ring is attached is kept surgically clean in order to prevent dermatitis which might result from contact of the skin with the waste material for a period of time. Also, it is important to prevent infection of the stoma which can lead to serious consequences. Should waste material be present on the skin prior to application of the adhesive for securing the ring, the skin-ring bond will fail, causing the waste receptacle and ring to loosen its attachment to the skin and spill its contents, in addition to causing dermatitis, infection or the like at the adhesive-skin interface. Thus, the adhesive serves as a sealant in the connection of the ostomy appliance to the stoma, as well as a bonding agent in the bag-ring-skin interface.

In the replacement of the ostomy appliance, the general procedure is first to remove the ring and the receptacle. A standard rolled 4×4 cotton gauze pad or tampon is then placed on top of the stoma to absorb any waste material and prevent it from leaking on the surrounding skin prior to the application of the adhesive. The surrounding skin must be cleaned and dried. This is generally accomplished by the use of a commercially available "prep" agent, which removes the skin oils, cleans, and leaves a dry skin surface. On the application of the adhesive, the gauze is removed from the stoma and a ring is placed over the stoma in a precisely centered position. Generally, one must remain in a standing position and using a mirror to achieve the centered position. The ostomy appliance is then attached to the ring and tightly secured to the skin.

In the past, the gauze has been rolled to such a size as will admit the ring to be placed over the stoma without prior removal of the gauze. Should the gauze be removed during the placement of the ring, waste material can leak out necessitating the recleaning of the entire skin area about the stoma and the entire procedure must be begun anew. It becomes apparent that in the replacement of an ostomy appliance that the ring must be centered on the stoma and that the area immediately surrounding the stoma and in contact with the ring must be clean and dry during the replacement of an ostomy appliance.

SUMMARY OF THE INVENTION

Therefore an object of the subject invention is a medical-surgical apparatus which will facilitate the replacement of a waste receptacle bag over a stoma.

Another object of the subject invention is a means of assuring the adhesion of the waste receptacle ring over a stoma of an individual having either a colostomy or a cystostomy.

A further object of the subject invention is a means for precisely and easily centering the sealing ring over the stoma while simultaneously keeping the skin area about the stoma dry and clean.

These and other objects are attained in accordance with the present invention wherein there is provided a hollow transparent cylindrical tube of an inexpensive material such as clear plastic which has an interior diameter slightly greater than the diameter of the stoma and an exterior diameter slightly smaller than the interior diameter of the waste receptacle ring. The tube is of a length that will premit easy handling and positioning over the stoma or, approximately three inches in the preferred embodiment.

In the use of the subject invention, the ostomy appliance is removed from the body and the skin area is cleaned and dried with an appropriate skin prep dressing. The cylinder of the subject invention is placed over the stoma and centered on the stoma. Because of the transparency of the cylinder, it may be easily positioned over the stoma and exactly centered without the use of a mirror or approximations. An absorbent material such as cotton or gauze is inserted in the cylinder for absorbing any waste matter leaking from the stoma into the tube. The skin area about the stoma is checked for cleanliness and dry condition and the adhesive is then applied. Some rings and waste receptacles have preapplied adhesive, in which case the protective backing is removed. A sealing ring may then be inserted onto the skin area over the cylinder. Due to the approximate conformity of the ring diameter with the cylinder diameter, the ring is automatically and accurately positioned over the stoma on the skin area. The cylinder is removed and the ostomy appliance attached to the ring.

DESCRIPTION OF THE DRAWINGS

Further objects of the invention, together with additional features contributing thereto and advantages accruing therefrom, will be apparent from the following description of one embodiment of the invention when read in conjunction with the accompanying drawings wherein:

FIG. 1 is a perspective view of the mid-section of a person having an ostomy appliance positioned over a stoma;

FIG. 2 is a perspective view showing the use of the inventive stoma centering apparatus of the subject invention during the cleaning of the skin area about the stoma;

FIG. 3 is a perspective view showing the sealing ring being centered over a stoma using the stoma centering device of the subject invention;

FIG. 4 shows the stoma centering apparatus of the subject invention in place permitting the sealing ring to be centered over the stoma; and, FIG. 5 is a cross section taken along the line 5—5 of FIG. 4.

Referring now to the drawings and in particular, to FIG. 1, there is shown a ostomy appliance or bag 15 in an operative, centered position over a stoma 20 (shown in dotted lines). This waste receptacle bag 15 has an opening 23 in communication with the stoma 20. This opening 23 is centered over the stoma 20 and the waste receptacle bag 15 is secured to hold this centered position by a waste receptacle ring appliance 16 (shown in dotted lines, FIG. 1). The waste receptacle bag 15 may be further supported by means of a belt 17 or any other suitable apparatus. The sealing ring 16 may be of any configuration and size and will be determined by the commercial ostomy appliance in use by the wearer.

In the removal and replacement of the waste receptacle bag 15, the old adhesive on the skin surface must be cleaned away and the area made clean and dry prior to replacement of the receptacle bag. The cleaning operation is demonstrated in FIG. 2. The waste receptacle bag 15 and ring 16 are first removed and the area then cleaned by the application of a skin prep dressing or the like with a cotton gauze material or tampon 25. In procedures of the prior art, after the area has been initially cleansed, a 4×4 piece of sterile gauze was rolled up and placed over the stoma 20. In the use of such a procedure, should the stoma leak excessively at this point, the gauze 25 may become saturated, leak itself and thereby require a fresh gauze dressing and require another complete cleaning of the entire area. By the use of the subject invention, the chance of such a leakage after cleaning is greatly reduced.

As shown in FIGS. 3 and 5, the subject invention comprises a transparent hollow cylinder open at both ends. The cylinder itself may be of glass, polycarbonate or similar relatively rigid transparent material and is generally of a size slightly larger than the stoma with which it is to be used; preferably the inside diameter of the cylinder will be approximately 1/16th of an inch larger than the stoma. After the removal of the full or used waste receptacle and initial cleaning of the skin area surrounding the stoma, the cylinder of the subject invention is held in place over the stoma as shown in FIGS. 2 and 3. Because of the transparency of the cylinder, it is easily positioned and centered over the stoma while standing or sitting and without the need for a mirror. Sterile cotton or other like absorbent material 26 may be inserted into the centered cylinder prior to the entire procedure or at this point so that it will absorb any waste matter being excreted from the stoma. In this manner, even if the preparation of the skin requires an excessive amount of time, causing the cylinder and absorbent material to absorb waste beyond their capacity, leakage of the stoma and cylinder will only occur away from the body and not on the skin area surrounding the stoma. The cylinder end opposite the stoma will allow the leakage of the waste at a point spaced from the body.

The skin is next checked for cleanliness and dry condition and the adhesive is applied to the cleansed skin area about the stoma and cylinder. The ring 16 is then placed over the cylindrical tube 21, and brought into contact with the skin and secured to the skin area about the stoma 20 through the adhesive 22. The cylinder 21 of the subject invention is then removed and the bag is attached to the ring and about the body, by the application of adhesive to the ring and the joining of the bag to the ring.

Of course, it is to be recognized that if waste receptacles and rings having preapplied adhesive are used, then the adhesive backing is removed and the attachment of the respective parts is attended to as above.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. The method of replacing a full or used ostomy appliance on a person having a stoma for the excretion of waste material from the body, comprising the steps of:
   a. removing said used ostomy appliance from the stoma;
   b. initially cleaning the skin area about the stoma;
   c. centering a hollow cylinder having an inside diameter slightly greater than the diameter of the stoma about the stoma and retaining said cylinder in a centered position;
   d. inserting an absorbent material into said cylinder for absorbing waste material excreted from said stoma;
   e. preparing the skin by cleaning and drying the skin area about the stoma with a skin prep agent while maintaining the cylinder in a sealing relationship about the stoma;
   f. applying an adhesive substance to said prepared skin;
   g. inserting a sealing ring over said cylinder and onto the skin for adherence to the skin; and,
   h. withdrawing said cylinder from the skin and adhering another ostomy appliance to said sealing ring.

2. The method of claim 1 wherein said hollow cylinder is a transparent material selected from the group of glass and polycarbonate.

3. The method of claim 1 wherein said hollow cylinder has an outside diameter less than the interior diameter of the sealing ring.

4. The method of claim 3 wherein said outside diameter of said cylinder is 1/16th of an inch less than the inside diameter of the sealing ring.

5. The method of claim 1 wherein said absorbent material is sterile cotton.

6. The method of claim 1 wherein said hollow cylinder is transparent and centering said cylinder is accomplished through said cylinder to visually align said cylinder on said stoma.

* * * * *